United States Patent [19]

Vazquez et al.

[11] Patent Number: 5,068,367

[45] Date of Patent: Nov. 26, 1991

[54] TETRACYANO-1,4-HYDROQUINONE AND TETRACYANO-1, 4-BENZOQUINONE

[75] Inventors: Carlos Vazquez, Newark, Del.; Joel S. Miller, West Chester, Pa.

[73] Assignee: E. I. Du Pont de Nemours and Company, Wilmington, Del.

[21] Appl. No.: 472,920

[22] Filed: Jan. 31, 1990

[51] Int. Cl.$^5$ .................. C07C 50/02; C07C 50/38
[52] U.S. Cl. .................................. 552/310; 552/309
[58] Field of Search .................. 552/306, 309, 310

[56] References Cited

U.S. PATENT DOCUMENTS 3,114,756  12/1963  Wallenfels et al. .............. 260/396
3,941,811   3/1976  Vighau ............................ 552/309

OTHER PUBLICATIONS

K. Wallenfels et al., Tetrahedron, 21 2239-2256 (1965).
Angew. Chem. 73, 142 (1961).
E. A. Braude et al., Journal of the Chemical Society (London) 1954, p. 3572.
L. Bucsis et al., Chemische Berichte, 109, 2462-2468 (1976).
O. W. Webster et al., J. Org. Chem 30, 3250 (1965).

*Primary Examiner*—C. Warren Ivy
*Assistant Examiner*—Raymond Covington

[57] ABSTRACT

Processes for the preparation of tetracyano-1,4-hydroquinone and its conversion to tetracyano-1,4-benzoquinone via a disilver salt are disclosed.

22 Claims, No Drawings

TETRACYANO-1,4-HYDROQUINONE AND TETRACYANO-1,4-BENZOQUINONE

FIELD OF THE INVENTION

This invention relates to improved processes for the preparation of tetracyano-1,4-benzoquinone and it's precursor tetracyano-1,4-hydroquinone.

BACKGROUND

U.S. Pat. No. 3,114,756 issued Dec. 17, 1963, discloses the composition of tetracyano-1,4-hydroquinone, a process for its preparation, the composition of tetracyano-1,4-benzoquinone and a process for its preparation from tetracyano,1,4-hydroquinone. The process leading to tetracyano-1,4-hydroquinone originates from 2,5-dicyano-3,6-dihalogeno-1,4-benzoquinones. It is stated that it is not possible to introduce further cyano groups into 2,3-dicyano-5,6-dihalogeno-1,4-benzoquinones or 2,3-dicyano-5,6-dihalogeno-1,4-hydroquinones. Since 2,3-dicyano-5,6-dichloro-1,4-hydroquinone is the product of the reaction of chloranil (tetrachloro-1,4-benzoquinone) with potassium cyanide, it is implied that chloranil would not be a suitable starting material for tetracyano-1,4-hydroquinone. The process for the conversion of tetracyano-1,4-hydroquinone to tetracyano-1,4-benzoquinone utilizes as reagent "nitrous gases." These same chemical conversions are discussed at length by K. Wallenfels et al., Tetrahedron, 21, 2239-2256 (1965) and Angew. Chem. 73, 142 (1961).

E. A. Braude et al., Journal of the Chemical Society (London) 1954, p 3572 disclose that attempts to replace the chlorine atoms in chloranil with cyanide groups from cuprous cyanide were unsuccessful.

L. Bucsis et al., Chemische Berichte, 109, 2462-2468 (1976) disclose the isolation of tetracyano-1,4-hydroquinone in 5% yield as a by-product in the preparation of 2,3-dichloro-5,6-dicyano-1,4-hydroquinone from the reaction of chloranil with potassium cyanide. It is stated that, despite the low yields, this route to tetracyano-1,4-hydroquinone is preferred over the route of Wallenfels et al. due to shorter cycle time and availability of starting materials. There is neither disclosure nor suggestion of how to convert this low-yield process to a high-yield reproducible process.

O. W. Webster et al., J. Org. Chem, 30, 3250 (1965), disclose the preparation of tetracyano-1,4-hydroquinone from tetracyano-p-phenylenediamine via the bis(-diazonium) compound in 35% yield. The tetracyano-p-phenylenediamine starting material was itself prepared in 3.7% yield from tetracyanoethane. Thus, there exists no easily operable, reasonable yield route to tetracyano-1,4-hydroquinone. Nor is there a known process for the conversion of tetracyano-1,4-hydroquinone to tetracyano-1,4-benzoquinone that involves the use of stable, readily available reagents. It is therefore an object of the present invention to provide a process for the preparation of tetracyano-1,4-hydroquinone.

It is a further object of the present invention to provide processes for the preparation of tetracyano-1,4-benzoquinone.

It is a further object of the present invention to provide novel electron-transfer complexes of tetracyano-1,4-benzoquinone.

SUMMARY OF THE INVENTION

This invention provides a novel process for the preparation of tetracyano-1,4-hydroquinone comprising reacting a tetrasubstituted-1,4-benzoquinone with a source of cyanide ion in a solvent comprising a lower alcohol selected for its ability to dissolve both the source of cyanide ion and the tetrasubstituted-1,4-benzoquinone starting material in a manner such that the cyanide ion is, at all stages of the reaction, present in stoichiometric excess.

This invention also provides a novel process for the conversion of tetracyano-1,4-hydroquinone to tetracyano-1,4-benzoquinone that comprises a) reacting tetracyano-1,4-hydroquinone with a silver salt to yield the disilver salt of tetracyano-1,4-hydroquinone, and b) reacting said disilver salt with an oxidizing agent to yield tetracyano-1,4-benzoquinone.

This invention also provides a novel process for the conversion of tetracyano-1,4-hydroquinone to tetracyano-1,4-benzoquinone that comprises a) reacting tetracyano-1,4-hydroquinone with a tetraalkyl or tetraaryl ammonium salt to yield the corresponding ammonium salt of tetracyano-1,4-hydroquinone; b) reacting said ammonium salt with a silver salt to yield the disilver salt of tetracyano-1,4-hydroquinone and c) reacting said disilver salt with an oxidizing agent to yield tetracyano-1,4-benzoquinone.

This invention also provides novel, easily characterizable 1:1 electron-transfer complexes of tetracyano-1,4-benzoquinone with electron donors, for example, with ferrocene, substituted ferrocenes, tetrachalcogenfulvalenes and substituted tetrachalcogenfulvalenes and also 1:1 charge-transfer complexes of tetracyano-1,4-benzoquinone with compounds such as triphenylene, hexaaminobenzene and hexamethoxybenzene.

DETAILED DESCRIPTION OF THE INVENTION

This invention provides improved yield process routes to the target compounds utilizing starting materials more readily available than those utilized in previously known routes. The reference by L. Bucsis et al. cites yields of tetracyano-1,4-hydroquinone from various substituted quinones in the following quantities: from 2,5-dibromo-3,6-dimethoxy-1,4-benzoquinone —3%; from 2,3-dichloro-5,6-dicyano-1,4-bezoquinone —3%; from chloranil—5%; from bromanil—7%. The yield of tetracyano-1,4-hydroquinone from various substituted quinones employing the process of this invention are approximately doubled versus the yields reported in the prior art, for example; from bromanil 18%; from 2,3-dichloro-5,6-dicyano-1,4-benzoquinone —6%.

The prior art route to tetracyano-1,4-benzoquinone from tetracyano-1,4-hydroquinone utilizes the rather obscure reagent "nitrous gases". The process of the present invention utilizes synthetic procedures easily explainable to and readily reproducible by one skilled in the art.

The processes of the present invention are summarized in reaction Scheme 1.

Scheme 1

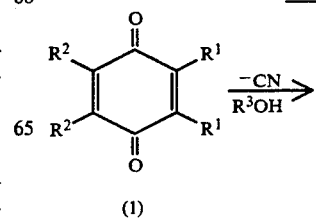

(1)

-continued
Scheme 1

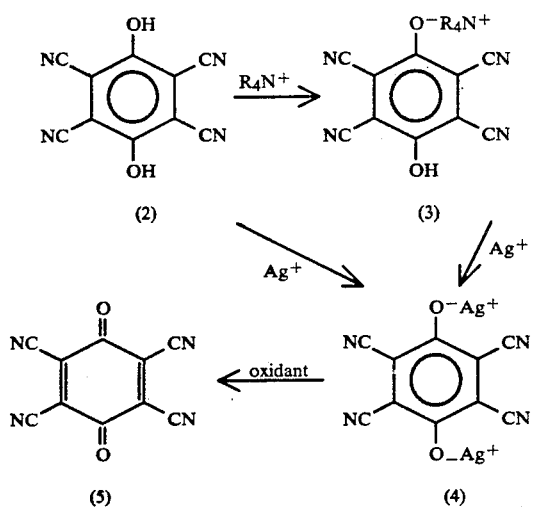

In Scheme 1, R signifies lower alkyl, containing up to about 8 carbon atoms; $R^1$ signifies cyano and $R^2$ signifies chloro, or $R^1$ equals $R^2$ and both are equal to bromo, chloro, or cyano. $R^3$ signifies a lower alkyl group containing up to about 4 carbon atoms.

For the first process of the present invention, the conversion of a tetrasubstituted-1,4-benzoquinone (1) to tetracyano-1,4-hydroquinone, (2) reaction conditions are important. Suitable tetrasubstituted-1,4-benzoquinones include bromanil, chloranil, 2,3,5,6-tetramethoxy-1,4-benzoquinone, and 2,3-dichloro-5,6-dicyano-1,4-benzoquinone. To secure the advantages of the present invention, it is preferred that the cyanide ion is always, and in all parts of the reaction media, in stoichiometric excess. This is most readily achieved by adding the tetrasubstituted-1,4-benzoquinone starting material to a solution of the cyanide ion source. Preferably, this addition is carried out relatively slowly; for example, in a preparation involving 25 grams of bromanil, the addition was carried out over about one hour.

The solvent for the reaction is preferably a lower alcohol of up to four carbon atoms, and most preferably methanol. The prime criterion for the solvent is that it provide at least some solubility for the source of cyanide ion and for the tetrasubstituted-1,4-benzoquinone starting material. It is preferable that the solvent be essentially free of water.

Temperature conditions for the reaction are not critical. The reaction is preferably carried out from about room temperature up to the boiling point of the solvent. Pressure limits for the reaction have not been explored. It is most convenient to carry out the reaction at ambient atmospheric pressure.

The source of cyanide ion can be any of a number of soluble cyanide salts, for example, alkali metal (lithium, sodium or potassium) cyanide or ammonium cyanides, for example, tetraalkyl or tetraaryl ammonium cyanides. The alkyl group present in the tetraalkyl ammonium cyanide can contain up to about 8 carbon atoms.

It is important that the cyanide ion is always in stoichiometric excess during the course of the reaction. That is, there must, in the case of, for example, bromanil, be at least greater than four moles of cyanide ion per mole of bromanil present during the course of the reaction. Preferably a greater excess is employed. Preferably, a two-fold excess is employed, that is, for each mole of bromanil, eight moles of cyanide would be employed.

Because of the tendency of the reaction that forms terracyano-1,4-hydroquinone to yield by-products or, in most cases, not to proceed to completion, the mode of isolation of the tetracyano-1,4-hydroquinone product is critical with regard to obtaining that product in a pure, readily characterizable form. Isolation and purification takes advantage of the propensity of tetracyano-1,4-hydroquinone toward salt formation and complex formation. For example, as described in example 1, the isolation and purification of tetracyano-1,4-hydroquinone proceeds via a morpholinium salt, a pyrene complex and a dioxane complex. The dioxane complex is then dissolved in water; the aqueous solution filtered to remove insolubles; the filtrate acidified to precipitate pure tetracyano-1,4-hydroquinone which may then be filtered or extracted with ether and recovered after evaporation of the ether.

The process of the present invention of converting tetracyano-1,4-hydroquinone (2) to its disilver salt (4) is carried out either directly, with no intervening isolation step or indirectly, via an isolated ammonium salt of tetracyano-1,4-hydroquinone (3).

In the direct route, a stoichiometric excess of a soluble silver salt is allowed to react with tetracyano-1,4-hydroquinone in the presence of a solvent. The silver salt may be, for example, silver triflate or silver nitrate. Silver nitrate is preferred.

Solvents suitable for use in this reaction include those capable of dissolving both the selected silver salt and the tetracyano-1,4-hydroquinone. Preferred solvents are methanol, acetonitrile, or water, with water being most preferred.

The temperature of the reaction is not critical, although when using certain solvents, heating may be desirable to speed the dissolution of reagents. The temperature range is from about room temperature to about the boiling point of the solvent. The reaction is typically carried out at atmospheric pressure under an air atmosphere, although the use of an inert gas atmosphere is not precluded.

A stoichiometric excess of the soluble silver salt is required. Typically an amount at least about twice that required by the reaction stoichiometry is used.

In the indirect conversion of tetracyano-1,4-hydroquinone (2) to its disilver salt (4), the tetracyano-1,4-hydroquinone is first converted to a monotetra-substituted ammonium salt (3), isolated as such, and is then converted further to the disilver salt.

This conversion, which involves the reaction of tetracyano-1,4-hydroquinone with a tetra-lower alkyl ammonium salt, where lower alkyl signifies an alkyl group that may contain up to about 8 carbon atoms, or a tetra-aryl ammonium salt, is carried out in a solvent capable of dissolving both reactants, for example water, a lower alkyl alcohol or acetonitrile. The preferred solvent is water.

The tetra-lower alkyl ammonium salt or a tetra-aryl ammonium salt, can possess essentially any counter anion. Halides, especially bromide or iodide, are preferred as the counter anion.

The temperature range employed is from approximately room temperature to the boiling point of the chosen solvent. The reaction is carried out at ambient pressure and can be carried out under an air atmosphere, although the use of an inert gas atmosphere is not precluded.

The tetra-lower alkyl ammonium salt or a tetra-aryl ammonium salt is employed in at least a stoichiometric amount, that is one mole of tetra-lower alkyl ammonium salt or tetraaryl ammonium salt, per mole of tetracyano-1,4-hydroquinone to yield the monoammonium salt.

The second step of this indirect conversion of tetracyano-1,4-hydroquinone to its disilver salt involves the conversion of the isolated tetra-lower alkyl ammonium salt or tetra-aryl ammonium salt. This reaction is similar to that described above for the direct conversion.

A stoichiometric excess of a soluble silver salt is allowed to react with the tetra lower-alkyl ammonium salt or tetra-aryl ammonium salt of tetracyano-1,4-hydroquinone in the presence of a solvent. The silver salt may be, for example, silver triflate or silver nitrate. Silver nitrate is preferred.

Solvents suitable for use in this reaction include those capable of dissolving both the selected silver salt and the tetra lower-alkyl ammonium salt or tetraaryl ammonium salt of tetracyano-1,4-hydroquinone. Preferred solvents are methanol, acetonitrile, or water with water being most preferred.

The temperature of the reaction is not critical, although when using certain solvents, heating may be desirable to speed the dissolution of reagents. The temperature range is from about room temperature to about the boiling point of the solvent. The reaction is typically carried out at atmospheric pressure under an air atmosphere, although the use of an inert gas atmosphere is not precluded.

A stoichiometric excess of the soluble silver salt is required. Typically an amount at least about twice that required by the reaction stoichiometry is used.

The final reaction step in the route from tetracyano-1,4-hydroquinone (2) to tetracyano-1,4-benzoquinone (5) is the conversion of the disilver salt of retracyano-1,4-hydroquinone (4), whether prepared by the direct or indirect route, to the tetracyano-1,4-benzoquinone (5) product.

This conversion is carried out by the oxidative action of an oxidizing agent on the disilver salt of tetracyano-1,4-hydroquinone in the presence of a solvent.

Solvents suitable for use in this reaction are organic solvents that are non-reactive to the oxidizing agent under the conditions of the oxidation reaction. This group of solvents includes, for example, ethylene dichloride, methylene chloride, carbon tetrachloride, hexane and other aliphatic hydrocarbons. In general, acceptable solvents have no site of unsaturation or other functionality capable of reacting with the oxidizing agent under the chosen reaction conditions. A preferred solvent is ethylene dichloride. The solvent is, preferably, free of water and oxygen.

Oxidizing agents suitable for use herein are halogens, for example chlorine, bromine, iodine, iodine monochloride, iodine monobromide, and bromine monochloride. Bromine is the preferred oxidizing agent. A driving force for the oxidation reaction is the formation and precipitation of silver halide.

The reaction temperature range is from about room temperature to the boiling point of the solvent. The reaction is carried out under atmospheric pressure. It is desirable to carry out the reaction under an atmosphere of an inert gas, for example, argon or nitrogen.

A further aspect of the present invention comprises 1:1 electron-transfer complexes of tetracyano-1,4-benzoquinone with electron donors, such as ferrocene, substituted ferrocenes, tetrachalcogenfulvalenes and substituted tetrachalcogenfulvalenes, and also 1:1 charge transfer complexes of tetracyano-1,4-benzoquinone with a substituted aromatic compound, such as triphenylene, hexaaminobenzene and hexamethoxybenzene.

The formation of charge transfer complexes and electron transfer complexes from tetracyano-1,4-benzoquinone and appropriate complexing compounds is carried out in an organic solvent selected for its ability to dissolve both the tetracyano-1,4-benzoquinone and the complexing compound, for example acetonitrile and tetrahydrofuran. The complex-forming reaction is carried out at ambient pressures in a temperature range from approximately room temperature to the boiling point of the solvent. The complex-forming reaction is carried out under an inert atmosphere, for example, under nitrogen or argon.

The utility of tetracyano-1,4-hydroquinone is as an intermediate to tetracyano-1,4-benzoquinone. The utility of tetracyano-1,4-benzoquinone is as a very strong oxidizing agent, a hydrogen abstraction reagent, and as a reagent in the formation of charge and electron transfer complexes. The strength of tetracyano-1,4-benzoquinone as a hydrogen abstraction (dehydrogenation) agent exceeds that of 2,3-dichloro-5,6-dicyano-1,4-benzoquinone (DDQ), the use of which is described by D. Walker et al., Chem. Rev. 1967, 67, 153 and H. D. Dieter et al., J. Org. Chem., 1980, 45, 1596. The charge electron transfer complexes are extremely stable and are therefore useful in the preparation of organic semiconductors.

The following examples illustrate the present invention, but are not intended to limit it in any manner. In the examples that follow, infrared spectra were recorded on a Nicolet 7199 Fourier transform spectrometer. Elemental analyses were performed by Oneida Research Services, Inc. (Whitesboro, N.Y.).

X-ray crystal structure analysis was carried out with an Enraf-Nonius CAD4 diffractometer using MoK$\alpha$ radiation.

EXAMPLES

Example 1

Preparation of tetracyano-1,4-hydroquinone from bromanil

Sodium cyanide (23 g; 0.472 mole) was dissolved in 2 L of methanol. 2,3,5,6-Tetrabromo-1,4-benzoquinone (bromanil, Lancaster Syntheses, Windham, NH) was added portionwise (25 g; 0.059 mol) over a period of about 1 hour. The temperature was allowed to rise to 34° C.; the mixture turned red. The solution was heated to reflux for 45 minutes, then cooled back to room temperature. HCl gas was bubbled in until the pH reached an indicated 0 to 1 and the mixture turned brown. The mixture was concentrated under vacuum to dryness, and the residue was extracted several times with 1 L of diethyl ether. Morpholine was added to the ethereal extract and the red morpholine salt that precipitated was collected, dried and recrystalized from methanol. There were recovered 12.5 g of the crude morpholine salt of tetracyano,1,4-hydroquinone. The morpholine salt was dissolved in the minimum amount of water, and HCl was bubbled in until the mixture turned yellow and a solid separated out. This mixture was extracted with ether. The ethereal extracts were combined, dried over magnesium sulfate, and evaporated to dryness to yield a yellow solid. This solid was then dissolved in 150 ml of water, and the aqueous suspension was filtered to separate insoluble portions. HCl was bubbled into the aqueous filtrate until a yellow, nicely crystalline solid separated. This mixture was extracted with ether. The ethereal extracts were combined, dried over magnesium sulfate, and evaporated to dryness to yield another yellow solid. This yellow solid was dissolved in hot acetic acid, and an equal amount of pyrene dissolved in methylene chloride was added. A red complex precipitated out which was collected, dried and treated with hot dioxane which resulted in the formation of a dioxane complex. The dioxane complex was dissolved in water, and the aqueous suspension was filtered to separate insolubles. HCl was bubbled into the aqueous filtrate until a yellow solid separated. This mixture was extracted with ether. The ethereal extracts were combined, dried over magnesium sulfate, and evaporated to dryness to yield another yellow solid. This was recrystallized from acetic acid to give yellow crystals (1.97 g, 16% yield). Analysis Calc'd for $C_{10}H_2N_4O_2$(Found) %C=57.15 (56.95), %H=0.95(0.95) %N=26.67(26.53), %O=15.24(15.37). Infrared $\nu$(CN) absorptions 2241 and 2263 cm$^{-1}$, $\nu$(OH) 3160br cm$^{-1}$; mp 373° C., with decomposition. The product in solution fluoresces yellow-green.

A repetition of this same procedure on the same scale afforded 2.23 g, 18% yield.

Example 2

Preparation of tetracyano-1,4-hydroquinone from bromanil

Reaction between bromanil (6.6 g, 0.0156 mol) and sodium cyanide (4.6 g, 0.0935 mol) in 500 ml of methanol was carried out essentially as described in example 1. There was isolated tetracyano-1,4-hydroquinone (0.31 g, 9% yield). Analysis Calc'd for $C_{10}H_2N_4O_2$(Found) %C =57.15 (56.89), %H=0.95(0.86) %N=26.67(26.17).

Example 3

Preparation of tetracyano-1,4-hydroquinone from 2,3-dichloro-5,6-dicyano-1,4-benzocuinone The reaction of 2,3-dichloro-5,6-dicyano-1,4-benzoquinone (10 g, 0.0441 mol) with sodium cyanide (9.3 g, 0.190 mol) was carried out in methanol (750 ml) essentially as described in example 1. There were obtained 0.56 g, 6% yield of yellow needles.

Example 4

Preparation of the disilver salt of tetracyano-1,4-hydroquinone from tetracyano-1,4-hydroquinone Tetracyano-1,4-hydroquinone (0.40 g, 0.0019 mol) was dissloved in hot water (25 ml). Silver nitrate (1.29 g, 0.0076 mol) in water (5 ml) was added all at once. The mixture turns black; a precipitate formed. Solid was collected and dried to give 0.79 g, 99% yield. Analysis Calc'd for $C_{10}N_4O_2Ag_2$ (Found) %C =28.34 (28.35), %H =0.00(0.14) %N=13.22.(13.27).

Example 5

Preparation of mono tetraethylammonium salt of tetracyano-1,4-hydroquinone

Tetracyano-1,4-hydroquinone (2.30 g, 0.0109 mol) was dissolved in 50 ml of hot water. Tetraethylammonium iodide (7.0 g, 0.027 mol) dissolved in 10 ml of hot water was added. The solution was heated to boiling for and the volume was reduced to about 10 ml. Long orange needles formed upon cooling which were collected and dried under vacuum to yield 2.61 g, 71% yield of tetraethylammonium tetracyano-1,4-benzeneoxide. Analysis Calc'd for $C_{18}H_{21}N_5O_2$. (Found) %C =63.70(63.75), %H=6.24(6.10) %N=20.64(20.69). Infrared(Nujol): $\nu$(CN) absorptions 2219 cm$^{-1}$, $\nu$(OH) 3515br cm$^{-1}$.

EXAMPLE 6

Preparation of mono tetramethylammonium salt of tetracyano-1,4-hydroquinone (as hydrate)

From tetracyano-1,4-hydroquinone (100 mg, 0.476 mmol) dissolved in 20 ml of hot water and tetramethylammonium bromide (60 mg, 1.05 mmol) dissolved in 10 ml of hot water, 90 mg of tetramethylammonium tetracyano-1,4-benzeneoxide monohydrate was prepared. Analysis Calc'd for $C_{14}H_{13}N_5O_2$. (Found) %C =55.86(56.25), %H =5.021(4.51) %N=23.24(23.17). Infrared $\nu$(CN) absorptions 2218 cm$^{-1}$ and 2224sh cm$^{-1}$.

Example 7

Preparation of the disilver salt of tetracyano-1,4-hydroquinone from tetraethylammonium tetracyano-1,4-benzeneoxide Tetraethylammonium tetracyano-1,4-benzeneoxide (0.82 g, 0.00175 mol) was dissolved in 30 ml of hot water and silver nitrate (1.19 g, 0.007 mol) dissolved in 10 ml of water was added all at once. The mixture turned black and a solid precipitated. The solid was collected while the mixture was still warm and was dried to give 0.70 g (69% yield) of the disilver salt. Analysis Calc'd for $C_{10}N_4O_2Ag_2$ (Found) %C=28.34(28.05), %H =(0.14) %N =13.22(12.90), %O=7.55(8.04). Infrared: $\nu$(CN) absorption 2229 cm$^{-1}$.

Example 8

Preparation of tetracyano-1,4-benzoquinone

Working under a nitrogen atmosphere, bromine (1.06 g, 0.0066 mol) dissolved in 1 ml of dichloromethane was added to a suspension of the disilver salt of tetracyano-1,4-hydroquinone (0.70 g, 0.00165 mol) in 40 ml of dichloromethane. After ½ hour agitation at room temperature, the formed silver bromide was filtered off under nitrogen, and the cake was washed three times with 30 ml of dichloromethane. The filtrate and washes were combined and evaporated to near dryness and cooled to room temperature whereupon small yellow needles separated. These were collected and dried to give 0.16 g (47% yield) of tetracyano-1,4-benzoquinone. Analysis Calc'd for $C_{10}N_4O_2$. (Found) %C=57.70(57.10), %H =0(0.27) %N=26.92(26.58), %O=15.37(15.95). Infrared: $\nu$(CN) absorption 2244w cm$^{-1}$, $\nu$CO 1698s cm$^{-1}$. X-ray crystal structure analysis confirmed the structure of neutral cyanil. There was no residual electron density suggesting hydroxyl hydrogens.

Example 9

Preparation of tetracyano-1,4-benzocuinone

In an improvement over the procedure of example 8, working under a nitrogen atmosphere, the disilver salt of tetracyano-1,4-hydroquinone (3.10 g, 0.0073 mol) was added all at once to a solution of bromine (4.68 g, 0.0293 mol) dissolved in 50 ml of dichloroethane. After one hour agitation at room temperature, the mixture was heated to reflux for 10 minutes to dissolve the organic product, and the silver bromide was filtered off hot under nitrogen. The cake was washed four times with 75 ml of hot dichloroethane, still under a nitrogen atmosphere. The filtrate and washes were combined and evaporated to dryness to give 0.97 g (65% yield) of tetracyano-1,4-benzoquinone.

Example 10

Preparation of Ferrocenium 1,4-tetracyanobenzoquinoneide (1:1)

To a solution of ferrocene (22.3 mg, 0.120 mmol) in 5 ml of dry acetonitrile was added a second solution of tetracyano-1,4-benzoquinone (25 mg, 0.120 mmol) in 5 ml of dry acetonitrile. The green mixture was chilled in a refrigerator and the precipitate that formed was collected and dried to yield 44 mg (94% yield) of black needles. Analysis Calc'd for $C_{20}H_{10}N_4O_2Fe$. (Found) %C = 60.94(60.75), %H = 2.56(2.50) %N = 14.21(13.88). Infrared (Nujol): $\nu$(CN) absorption 2220 cm$^{-1}$.

Examples 11–19

1:1 Complex formation

Using procedures similar to example 10, 1:1 complexes between tetracyano-1,4-benzoquinone and the indicated complexing compounds were prepared.

with tetracyano-1,4-benzoquinone (40 mg; 0.192 mmol) also dissolved in 1 mL dry acetonitrile. After reducing the volume in half and cooling to −20° C. crystals precipitated and were collected. The infrared spectra of the precipitate was identical to that obtained from a mixture of authentic anthracene and tetracyano-1,4-hydroquinone ($\nu$(C≡N)=2239 and 2263 cm$^{-1}$) verifying that tetracyano-1,4-benzoquinone dehydrogenates 9,10-dihydroanthracene.

Example 22

Tetracyano-1,4-benzoquinone as hydrogen abstraction reagent

A solution of 2,3-dichloro-5,6-dicyanohydroquinone ($H_2DDQ$) (83 mg; 0.36 mmol) dissolved in 5 mL dry acetonitrile was reacted with tetracyano-1,4benzoquinone (75 mg; 0.36 mmol) also dissolved in 3 mL dry acetonitrile. After reducing the volume and cooling to −20° C. crystals precipitated and were collected. The infrared and VIS-UV spectra of the precipitate were as expected for tetracyano-1,4-hydroquinone ($\nu$(C≡N) =2241 and 2264 cm$^{-1}$) verifying that tetracyano-1,4-benzoquinone dehydrogenates 2,3-dichloro-5,6-dicyanohydroquinone and is a stronger hydrogen abstraction reagent than 2,3-dichloro-5,6-dicyanobenzoquinone (DDQ).

What is claimed is:

1. A process for the preparation of tetracyano-1,4-

|  |  | Analysis Calc'd (Found) | | | |
|---|---|---|---|---|---|
| Complexing agent | Product formula | C | H | N | O |
| 11-octamethylferrocene | $C_{28}H_{32}N_4O_2Fe$ | 66.41 | 5.17 | 11.07 | |
|  |  | 66.45 | 5.35 | 11.04 | |
| 12-decamethylferrocene | $C_{30}H_{30}N_4O_2Fe$ | 67.43 | 5.66 | 10.49 | 5.99 |
|  |  | 66.96 | 5.30 | 10.37 | 6.20 |
| 13-tetrathiafulvalene | $C_{16}H_4N_4O_2S_4$ | 46.59 | 0.98 | 13.58 | |
|  |  | 46.34 | 0.89 | 13.31 | |
| 14-N,N,N',N'-tetra-methyl-p-phenylene diamine | $C_{20}H_{16}N_6O_2$ | 64.51 | 4.32 | 22.57 | |
|  |  | 64.40 | 4.36 | 22.19 | |
| 15-decamethyl-cobaltocene | $C_{30}H_{30}N_4O_2Co$ | 67.03 | 5.63 | 10.40 | |
|  |  | 67.13 | 5.20 | 9.52 | |
| 16-hexaazaoctadeca-hydrocoronene | $C_{28}H_{24}N_{10}O_2$ | 63.14 | 4.54 | 26.31 | |
|  |  | 63.02 | 4.72 | 26.26 | |
| 17-triphenylene | $C_{18}H_{12}N_4O_2$ |  |  |  | |
| 18-hexaaminobenzene | $C_{16}H_{12}N_{10}O_2$ | 51.06 | 3.22 | 37.23 | |
|  |  | 51.05 | 3.09 | 35.15 | |
| 19-hexamethoxybenzene | $C_{22}H_{18}N_4O_8$ |  |  |  | |

Example 20

2:1 complex of decamethylcobaltocene with tetracyano-1,4-benzoquinone

The same general procedure as that for the 1:1 complexes was followed except for the mole ratio of the reactants. Decamethylcobaltocene (75 mg, 0.228 mmol) was allowed to complex with tetracyano-1,4-benzoquinone (24 mg, 0.114 mmol). There was obtained 64 mg (65% yield) of the 2:1 complex. Analysis Calc'd for $C_{50}H_{60}N_4O_2Co_2$. (Found) %C = 69.27(68.96), %H = 6.98(6.79), %N = 6.46(6.85), %O = 3.69(4.04). Infrared (Nujol): $\nu$(CN) absorption 2181s and 2194m cm$^{-1}$.

Example 21

Tetracyano-1,4-benzoquinone as hydrogen abstraction reagent

A solution of 9,10-dihydroanthracene (35 mg; 0.192 mmol) dissolved in 1 mL dry acetonitrile was reacted benzoquinone comprising:
(a) reacting tetracyano-1,4-hydroquinone with an excess of a silver salt to yield the disilver salt of tetracyano-1,4-hydroquinone; and
(b) reacting said disilver salt with an oxidizing agent to yield tetracyano-1,4-benzoquinone.

2. The process of claim 1 wherein the silver salt is silver nitrate.

3. The process of claim 1 wherein reaction step (a) is conducted in a solvent comprising methanol, acetonitrile or water.

4. The process of claim 1 wherein reaction step (a) is conducted in water.

5. The process of claim 1 wherein the oxidizing agent comprises chlorine, bromine, iodine, iodine monochloride, iodine momobromide or bromine monochloride.

6. The process of claim 5 wherein the oxidizing agent is bromine.

7. The process of claim 1 wherein reaction step (b) is conducted in a solvent comprising ethylene dichloride, methylene chloride, carbon tetrachloride or hexane.

8. The process of claim 7 wherein the solvent is ethylene dichloride.

9. The process of claim 7 wherein the solvent is methylene chloride.

10. A process for the preparation of tetracyano-1,4-benzoquinone comprising:
   (a) reacting tetracyano-1,4-hydroquinone with a tetra-alkyl or tetra-aryl ammonium salt to yield the corresponding ammonium salt of tetracyano-1,4-hydroquinone.
   (b) reacting said ammonium salt with an excess of a silver salt to yield the disilver salt of tetracyano-1,4-hydroquinone; and
   (c) reacting said disilver salt with an oxidizing agent to yield tetracyano-1,4-benzoquinone.

11. The process of claim 10 wherein the tetraalkyl ammonium salt contains up to 8 carbon atoms.

12. The process of claim 10 wherein the tetraalkyl or tetra-aryl ammonium salt comprises a halide salt.

13. The process of claim 12 wherein the salt is a bromide or iodide salt.

14. The process of claim 10 wherein at least one mole of tetra-alkyl or tetra-aryl ammonium salt is reacted per mole of tetracyano-1,4-hydroquinone.

15. The process of claim 14 wherein an excess of the ammonium salt is employed.

16. The process of claim 10 wherein reaction steps (a) and (b) are conducted in water.

17. The process of claim 10 wherein the silver salt comprises silver nitrate.

18. The process of claim 10 wherein the oxidizing agent comprises chlorine, bromine, iodine, iodine monochloride, iodine monobromide or bromine monochloride.

19. The process of claim 18 wherein the oxidizing agent is bromine.

20. The process of claim 10 wherein reaction step (c) is conducted in a solvent comprising ethylene dichloride, methylene chloride, carbon tetrachloride or hexane.

21. The process of claim 20 wherein the solvent is ethylene dichloride.

22. The process of claim 20 wherein the solvent is methylene chloride.

* * * * *

UNITED STATES PATENT AND TRADEMARK OFFICE
CERTIFICATE OF CORRECTION

PATENT NO. : 5,068,367
DATED : NOVEMBER 26, 1991
INVENTOR(S) : CARLOS VAZQUEZ

It is certified that error appears in the above-identified patent and that said Letters Patent is hereby corrected as shown below:

On the Title Page, item (19), after "Vazquez," please delete -- et al.--.

On the Title Page, item (75) after "Del.;", please delete --Joel S. Miller, West Chester, Pa. --.

Signed and Sealed this

Twenty-third Day of March, 1993

Attest:

STEPHEN G. KUNIN

*Attesting Officer*         *Acting Commissioner of Patents and Trademarks*